United States Patent [19]

Ohkouchi et al.

[11] Patent Number: 5,472,972

[45] Date of Patent: Dec. 5, 1995

[54] AGROCHEMICAL COMPOSITIONS AND METHODS EMPLOYING HYMEXAZOL AND 1,2-BENZISOTHIAZOLIN-3-ONE

[75] Inventors: Takeo Ohkouchi; Hitoshi Hosoda; Kenji Yasui; Shigehiro Kato; Yasuhiko Kondo; Yukiyoshi Takahi, all of Shiga, Japan

[73] Assignee: Sankyo Company, Limited, Tokyo, Japan

[21] Appl. No.: 271,264

[22] Filed: Jul. 6, 1994

Related U.S. Application Data

[63] Continuation of Ser. No. 55,516, Apr. 28, 1993, abandoned.

[30] Foreign Application Priority Data

| May 7, 1992 | [JP] | Japan | 4-114808 |
| Mar. 3, 1993 | [JP] | Japan | 5-042523 |

[51] Int. Cl.$^6$ ........................................ A01N 43/80
[52] U.S. Cl. ............................. 514/373; 514/380
[58] Field of Search ................... 514/373, 380; 548/243

[56] References Cited

U.S. PATENT DOCUMENTS

| 4,749,642 | 6/1988 | Kurematsu et al. | 430/372 |
| 5,219,875 | 6/1993 | Sherba et al. | 514/373 |

FOREIGN PATENT DOCUMENTS

| 2088407 | 1/1972 | France . |
| 3609939 | 10/1987 | Germany . |
| 17-2440 | 2/1942 | Japan . |
| 48-38148 | 11/1973 | Japan . |
| 49-22821 | 6/1974 | Japan . |
| 49-25470 | 7/1974 | Japan . |
| 49-40933 | 11/1974 | Japan . |
| 1113618 | 5/1968 | United Kingdom . |
| 1199737 | 7/1970 | United Kingdom . |
| 1256835 | 12/1971 | United Kingdom . |

OTHER PUBLICATIONS

"Hymexazol, A New Plant Protecting Agent", Ann. Sankyo Res. Lab. 25, pp. 1–51 (1973).
Central Patents Index, Basic Abstracts Journal, Section Ch, Week 7433, Derwent Publications Ltd., London, GB; of JP–A–49 001 728, 9 Jan. 1974.
Central Patents Index, Basic Abstracts Journal, Section Ch, Week 8135, 21 Oct. 1981, Derwent Publications Ltd., London, GB; Class C02, of JP–A–56 087 506, 16 Jul. 1981.
Central Patents Index, Basic Abstracts Journal, Section Ch, Week 8133, 7 Oct. 1981, Derwent Publications, Ltd., London GB; Class C03, of JP–A–56 079 605, 30 Jun. 1981.
Central Patents Index, Basic Abstracts Journal, Section Ch, Week 7448, Derwent Publications Ltd., London, GB; of JP–A–74 040 933, 6 Nov. 1974.
Sankyo Review Article, "Hymexazol, A New Plant Protecting Agent". Ann Sankyo Res. Lab 25:1–51, 1973.

*Primary Examiner*—S. Mark Clardy
*Attorney, Agent, or Firm*—Frishauf, Holtz, Goodman, Langer & Chick

[57] ABSTRACT

A combination of 3-hydroxy-5-methylisoxazole with an antimicrobial agent has good agricultural fungicidal activity which lasts longer than 3-hydroxy-5-methylisoxazole alone. The dihydrate of the calcium salt of 3-hydroxy-5-methylisoxazole has advantages over the free 3-hydroxy-5-methylisoxazole, other salts and the anhydrous compound.

8 Claims, No Drawings

AGROCHEMICAL COMPOSITIONS AND METHODS EMPLOYING HYMEXAZOL AND 1,2-BENZISOTHIAZOLIN-3-ONE

This application is a Continuation of application Ser. No. 08/055,516, filed Apr. 28, 1993, now abandoned.

BACKGROUND TO THE INVENTION

The present invention relates to certain new compositions and methods employing the known soil fungicide and plant growth regulator, 3-hydroxy-5-methylisoxazole, including, inter alia, a specific hydrate of the calcium salt of this compound.

3-Hydroxy-5-methylisoxazole, which is also known by the common name "hymexazol" and is sold by Sankyo Co. Ltd. under the trade name "Tachigaren", is disclosed, inter alia, in British Patent Specification No. 1 113 618. Subsequent British Patent Specifications No. 1 199 737 and 1 256 835 disclose other methods of preparing it and disclose its alkali metal salts. Japanese Patent Applications No. Sho 45-38953, Sho 45-72625, Sho 39-73350, Sho 45-29263 and Sho 45-108798 disclose various specific uses for this compound for the treatment or prevention of various plant diseases or as a plant growth regulator; these applications also disclose the calcium salt of 3-hydroxy-5-methylisoxazole as being especially useful, although no disclosure is made of any hydrate of the compounds. A complete review of the uses and activities of 3-hydroxy-5-methylisoxazole appears in Ann. Sankyo Res. Lab., 25, 1–51 (1973).

Soil-borne diseases affecting various kinds of crops and caused by soil-inhabiting pathogens have resulted in major problems for a long time in crop culture and agricultural administration, because they cause considerable damage and because they are difficult to control adequately. These problems have been made worse by the tendency, in recent years, to adopt schemes of intensive or mono-culture which result in a single type of crops being cultivated for many years continuously on the same soil, either in greenhouses or in open fields. As a consequence, occurrences of soil-borne diseases have greatly increased, and these have resulted in much damage and financial losses, since they can lead to a reduced or non-existent harvest. Typical soil inhabiting pathogens causing such soil-borne diseases include microorganisms belonging to the genera Fusarium, Pythium, Aphanomyces and Rhizoctonia.

3-Hydroxy-5-methylisoxazole is at present widely used to prevent a wide range of soil-borne diseases caused by such soil inhabiting pathogens because it is both effective and highly safe. For example, it is used, inter alia, for the prevention of seedling damping-off of rice and other crops caused by Pythium and Fusarium spp., Fusarium wilts of various crops caused by Fusarium sp. and sugar beat damping-off caused by Aphanomyces sp. 3-Hydroxy-5-methylisoxazole can prevent these soil-borne diseases not only by direct application to the soil treatment but also by treatment of seeds of potentially affected plants. For example, seed treatment with 3-hydroxy-5-methylisoxazole will very effectively control seedling damping off of sugar been caused by Aphanomyces and Pythium sp. Accordingly, a seed dressing of 3-hydroxy-5-methylisoxazole is widely used in Japan and in many European countries. In addition 3-hydroxy-5-methylisoxazole is known to have some physiological effects on various crop plants. For example, it will promote the growth of roots and will enhance the physiological activities of roots. Accordingly, it is very common in Japan to treat rice seeds with 3-hydroxy-5-methylisoxazole prior to sowing them in flooded paddy fields; and it is known that this treatment is effective to stabilize the establishment of rice seedlings.

Furthermore, when 3-hydroxy-5-methylisoxazole and/or salts thereof are used in hydroponics, they show an algicidal effect against, for example, pond scum.

The calcium salt of 3-hydroxy-5-methylisoxazole is known, as mentioned in Japanese Patent Application Kokai No. Sho 48-38148, to have similar activities to 3-hydroxy-5-methylisoxazole itself against plant diseases affecting various kinds of crops. In addition, since the calcium salt of 3-hydroxy-5-methylisoxazole has a lower volatility than 3-hydroxy-5-methylisoxazole, the salt has practical advantages when used for seed treatment.

In soil, however, 3-hydroxy-5-methylisoxazole is rapidly decomposed by soil microorganisms. This is a factor which limits its residual effectiveness, as reported in Ann. Sankyo Res. Lab. 25, 42–45.

If the dose of 3-hydroxy-5-methylisoxazole is greatly increased in order to prolong the residual effectiveness, phytotoxicity, such as growth inhibition or delayed germination, may occur on the treated plant, especially with seed treatment. The calcium salt of 3-hydroxy-5-methylisoxazole is, in this respect also, better than 3-hydroxy-5-methylisoxazole, because the phytotoxicity caused by the calcium salt with seed treatment is lower than that caused by 3-hydroxy-5-methylisoxazole. However, if used in a large amount, even the calcium salt sometimes causes phytotoxicity. It is, therefore, difficult to prolong the residual effectiveness by much increasing the amount of 3-hydroxy-5-methylisoxazole or of its calcium salt. Despite the usefulness of 3-hydroxy-5-methylisoxazole and derivatives thereof, there is, therefore, a need to improve the residual effectiveness of these compounds.

Hitherto, it has been considered an advantage of 3-hydroxy-5-methylisoxazole and derivatives thereof that these compounds are readily decomposed in the soil, ultimately to carbon dioxide, thus leaving few residues and reducing take-up by the plants, which could lead to incorporation of the compounds in the food chain. Such incorporation is always thought to be best avoided even though these compounds are notably non-toxic to animals, including humans.

We have now, however, surprisingly found that the administration of an antimicrobial agent in association with 3-hydroxy-5-methylisoxazole or a salt thereof will inhibit decomposition of the 3-hydroxy-5-methylisoxazole and prolong its period of effectiveness, without ultimately preventing that decomposition, thus maintaining the known safety advantages of these compounds. Furthermore, we have found that the improvement in the residual activity in the soil is greater than could be predicted simply from the inhibition of decomposition of the compound.

We have also discovered that the hitherto unknown dihydrate of the calcium salt of 3-hydroxy-5-methylisoxazole has particular advantages over the 3-hydroxy-5-methylisoxazole itself and its known salts, as explained in detail hereafter.

BRIEF SUMMARY OF INVENTION

Accordingly, in one aspect, the present invention provides a soil fungicidal composition comprising 3-hydroxy-5-methylisoxazole or a salt thereof in admixture with or in association with an antimicrobial agent.

In another aspect, the present invention provides, as a new composition of matter, the dihydrate of the calcium salt of 3-hydroxy-5-methylisoxazole.

DETAILED DESCRIPTION OF INVENTION

3-Hydroxy-5-methylisoxazole may be represented by the formula (I):

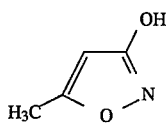
(I)

In the first aspect of the present invention, it is possible to use either 3-hydroxy-5-methylisoxazole itself or a salt thereof. Where a salt is used, the nature of the salt is not critical to the present invention, and any agriculturally acceptable salt may be employed, as is well known in the art. Examples of suitable salts include those described in Japanese Patent Application Kokai No. Sho 48-38148, especially metal salts or ammonium salts, for example: alkali metal salts, such as the sodium or potassium salts; alkaline earth metal salts, such as the calcium salt; other metal salts, such as the magnesium salt; and the ammonium salt. Of these, we particularly prefer the calcium salt, and most especially the dihydrate of the calcium salt of 3-hydroxy-5-methylisoxazole. In these salts, a metal atom or ammonium is substituted for the hydrogen atom of the hydroxy group at position 3 on the isoxazole ring of 3-hydroxy-5-methylisoxazole.

Thus, for example, the dihydrate of the calcium salt of 3-hydroxy-5-methylisoxazole may be represented by the formula (II):

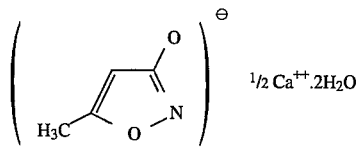
(II)

The dihydrate of the calcium salt of 3-hydroxy-5-methylisoxazole can be prepared by reacting a calcium compound with 3-hydroxy-5-methylisoxazole, and then recovering the desired calcium salt of 3-hydroxy-5-methylisoxazole under conditions favoring the formation of the dihydrate. For example, it may be obtained by the following procedure: one part (molar) of calcium hydroxide and 2 parts (molar) of 3-hydroxy-5-methylisoxazole are added to water and dissolved at a relatively high temperature, preferably from 70° to 90° C., more preferably approximately 80° C.; the resulting solution is then filtered whilst still warm, after which the filtrate is cooled to a suitable temperature to promote the formation of crystals of the dihydrate, suitably approximately 0° C.; the depositing crystals are then removed by filtration and dried, for example at 50°–60° C.

It should, however, be noted that these conditions are given only by way of example and that the reaction and separation conditions may be varied widely. The process of the present invention embraces all conditions which will produce the desired dihydrate.

In the first aspect of the present invention, the 3-hydroxy-5-methylisoxazole or salt thereof is employed in admixture with or in association with an antimicrobial agent. The nature of the antimicrobial agent will, of course, affect the longevity of the composition of the present invention. However, it may be selected from a wide range of such compounds using criteria well recognised in the art. We prefer to use an antibacterial or antifungal compound which is known to be very safe for industrial use, or a bactericidal or fungicidal compound known for agricultural use. Examples of suitable antimicrobial agents include: aldehydes and compounds capable of releasing aldehydes during use (i.e. when applied to the soil, water, plants, plant material or other material to be treated), alcohols including halogen-substituted nitro-alcohol derivatives and alcohols having an aryl substituent, quaternary ammonium salts, lipophilic weak acids (including benzoic acid, substituted benzoic acids, esters of these acids and phenols), thiazole derivatives (including isothiazolones), epoxides, substituted benzene and pyridine derivatives (especially the halogenated derivatives), compounds capable of releasing carbon disulfide during use including the tetrahydrothiadiazine thiones, guanidines and biguanides, antimicrobial halogen-substituted amides, organic and inorganic copper compounds, arsenic compounds including arsines, and various other antimicrobial agents including other fungicides and anthelmintics. Specific examples of such compounds include:

aldehydes:
especially dialdehydes, such as glyoxal, succinic dialdehyde and 1,5-pentanedial;

aldehyde releasing compounds:
that is compounds which release an aldehyde, especially formaldehyde, during use, for example, 2,5-dimethoxytetrahydrofuran, 5-halo-5-nitrodioxanes (such as 5-bromo-5-nitrodioxane), 2-halo-N-hydroxymethylacetamides (such as 2-chloro-N-hydroxymethylacetamide), 1-hydroxymethyl-5,5-dimethylhydantoin, hexamethylenetetramine, 1-(3-haloallyl)-3,5,7-triaza-1-azoniaadamantane halides [such as 1-(3-chloroallyl)-3,5,7-triaza-1-azoniaadamantane chloride], 1,3-bis(hydroxymethyl)-5,5-dimethyl-2,4-imidazolidinedione, 4,4-dimethyl-1,3-oxazolidine and hexahydro-1,3,5-tris(2-hydroxyethyl)-S-triazine;

halogen-substituted nitro-alcohol derivatives:
for example compounds of formula

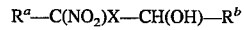

in which X represents a halogen atom, preferably a chlorine or bromine atom, $R^a$ and $R^b$ are the same or different and each represents an alkyl group having from 1 to 6 carbon atoms, preferably from 1 to 3 carbon atoms, a hydroxy group, a hydrogen atom or a halogen atom, such as 2-bromo-2-nitro-1,1-propanediol;

quaternary ammonium salts:
especially compounds of formula

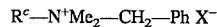

in which X represents a halogen atom, preferably a chlorine atom, Ph represents a phenyl group, and $R^c$ represents an alkyl group having from 1 to 20, preferably from 8 to 18, and more preferably from 12 to 14, carbon atoms, and more preferably a benzalkonium halide in which $R^c$ represents a mixture of alkyl groups having from 12 to 14 carbon atoms;

alcohols having an aryl substituent:
especially alcohols having from 1 to 6, more preferably from 1 to 4 carbon atoms, which are substituted by at least one aryloxy or benzyloxy group, such as benzyloxymethanol;

lipophilic weak acids:
  for example,
    benzoic acid and substituted benzoic acids (preferably hydroxy-substituted benzoic acids) and esters of these acids; examples of esters include the alkyl esters having from 1 to 10 carbon atoms, such as the methyl, ethyl, propyl, butyl, heptyl, octyl and 2-ethylhexyl esters, and aralkyl esters in which an alkyl group having from 1 to 4 carbon atoms is substituted by at least one (and preferably from 1 to 3) aryl groups, preferably phenyl groups, such as benzyl esters; and
    phenols, especially those in which phenol is substituted by at least one further aryl, preferably phenyl, group, such as o-phenylphenol;

isothiazolones:
  for example, isothiazol-3(2H)-one, 1,2-benzisothiazol-3(2H)-one, 5-halo-2-methylisothiazol-3(2H)-ones [such as 5-chloro-2-methylisothiazol-3(2H)-one], and 2-alkylisothiazol-3(2H)-ones in which the alkyl group has from 1 to 10 carbon atoms [such as 2-methylisothiazol-3(2H) one];

benzene and pyridine derivatives containing halogen atoms:
  for example 2,4,5,6-tetrahaloisophthalonitriles (such as 2,4,5,6-tetrachloroisophthalonitrile), haloxylenols, especially p-halo-m-xylenols (such as p-chloro-m-xylenol) and halocresols, especially p-halo-o-cresols and p-halo-m-cresols (such as p-chloro-o cresol and p-chloro-m-cresol);

carbon disulfide releasing compounds:
  that is compounds which release carbon disulfide during use, such as tetrahydro-3,5-dimethyl-2H-1,3,5-thiadiazine-2-thione, bis(dimethylthiocarbamoyl) disulfide and salts, especially alkali metal salts, of N-methyldithiocarbamic acid, such as sodium N-methyldithiocarbamate;

guanidines and biguanides:
  for example alkylguanidines, in which the alkyl part has from 1 to 20, preferably from 10 to 20, carbon atoms, such as dodecylguanidine, and bis [5-(halophenyl)biguanido]hexane dihydrohalides {such as bis[5-(p-chlorophenyl)biguanido]hexane dihydrochloride};

halogen-substituted amides:
  especially fatty acid amides, for example haloacetamides (such as chloroacetamide or bromoacetamide) and 2,2-dihalo-3-nitrilopropionamides (such as 2,2-dibromo-3-nitrilopropionamide);

copper compounds:
  such as cupric hydroxide, copper sulfate and copper-8-quinolate;

arsine compounds:
  such as 10,10'-oxybis-10H-phenoxarsine;

other antimicrobial agents, including other fungicides and anthelmintics:
  such as 2-(4-thiazolyl)-1H-benzimidazole, N-(dichlorofluoromethylthio)phthalimide and N,N-dimethyl-N'-(dichlorofluoromethylthio)sulfamide.

Of these, we prefer:
1,5-pentanedial (hereinafter referred to as Compound B-1),
2,5-dimethoxytetrahydrofuran (hereinafter referred to as Compound B-2),
glyoxal (hereinafter referred to as Compound B-3),
benzalkonium chloride (hereinafter referred to as Compound B-4),
1,2-benzisothiazolin-3-one (hereinafter referred to as Compound B-5),
cupric hydroxide (hereinafter referred to as Compound B-6),
4-chloro-2-xylenol (hereinafter referred to as Compound B-7),
4-chloro-2-cresole (hereinafter referred to as Compound B-8),
p-hydroxybenzoic acid esters, for example the alkyl esters in which the alkyl part has from 1 to 6 carbon atoms (for example the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups, of which we prefer those alkyl groups having from 1 to 4 carbon atoms, preferably the methyl, ethyl, propyl and butyl groups, and most preferably the propyl group), benzyl esters and aryl esters, particularly the phenyl ester; p-hydroxybenzoic acid is hereinafter referred to as Compound B-9, and
tetrahydro-3,5-dimethyl-2H-3,5-thiadiazine-2-thione (hereinafter referred to as Compound B-10).

The most preferred antimicrobial agents are Compound B-1 and Compound B-5. It is possible, in accordance with the present invention, to use a single one of these antimicrobial agents or to use a combination of two or more of them.

There is no particular restriction on the relative amounts of the 3-hydroxy-5-methylisoxazole or salt thereof and the antimicrobial agent, and the realtive amounts can range from, for example, 99:1 to 1:99 by weight. However, we prefer that the weight ratio of the amount of 3-hydroxy-5-methylisoxazole or salt thereof to the antimicrobial agent should be from 15:1 to 1:2, more preferably from 13:1 to 1:1 by weight.

It will, of course, be appreciated that the two main active compounds in the composition of the present invention can, and preferably are, supplied to the end user in admixture. However, this is not essential and the benefits of the invention will also be achieved if these two components are supplied separately and applied together. Accordingly, the present invention also embraces the concurrent or essentially concurrent use of 3-hydroxy-5-methylisoxazole or a salt thereof and the antimicrobial agent for the treatment of soil, plants water or parts, especially the reproductive matter, of plants, as well as the concurrent or effectively concurrent supply of 3-hydroxy-5-methylisoxazole or a salt thereof and the antimicrobial agent for the treatment of soil, plants water or parts, especially the reproductive matter, of plants.

Reflecting the activity of the compositions of the present invention, the invention further provides formulations which contain the compositions of the invention, together with a carrier and optionally other auxiliary agents, if necessary. These compositions may be formulated as preparations of the type commonly employed for agricultural or horticultural use, for instance as dusts, coarse dusts, microgranules, fine microgranules, wettable powders, and various liquid formulations, such as emulsifiable concentrates and aqueous or oily suspensions.

The carrier employed in such compositions may be natural or synthetic and organic or inorganic; it is generally employed to assist the active ingredient to reach the substrate to be treated, and to make it easier to store, transport or handle the active compound. It may be solid or liquid.

Suitable solid carriers include:

inorganic substances, such as clays (examples of which are bentonite, kaolinite, montmorillonite and attapulgite), talc, mica, agalmatolite, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as nut shells (e.g. of walnuts or other nuts), soybean meal, tobacco powder, walnut powder, wheat flour, wood meal, starch and crystalline cellulose; synthetic or natural high molecular weight polymers, especially resins, such as cumarone resins, petroleum resins, alkyd resins, polyvinyl chloride, polyalkylene glycols, ketone resins, ester gums, xanthan gum, copal gum and dammar gum; waxes such as carnauba wax and beeswax; or urea.

Examples of suitable liquid carriers include:

paraffinic or naphthenic hydrocarbons, such as kerosene, mineral oil, spindle oil and white oil; aromatic hydrocarbons, such as benzene, toluene, xylene, solvent naphtha, ethylbenzene, cumene and methylnaphthalene; halogenated hydrocarbons, especially chlorinated hydrocarbons, such as carbon tetrachloride, chloroform, trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, ethanol, isopropanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide and dimethyl sulfoxide; and water.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes of surface active agent (non-ionic, anionic, cationic or amphoteric) may be employed, but it is preferred to employ non-ionic and/or anionic surface active agents whereby wetting, adhesion and absorption and desired effects may be improved.

Examples of suitable non-ionic surface active agents include:

polyoxyethylene alkyl ethers, polyoxyethylene alkylallyl ethers, oxyethylene/oxypropylene block polymers, the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid; the polymerization adducts of ethylene oxide with amines, such as dodecylamine; amides or ethoxylated amides of higher fatty acids, such as stearamide; higher fatty acid esters of polyhydric alcohols, such as sorbitan, and the polymerization adducts of ethylene oxide therewith; higher fatty acid esters of glycerol borates or of ethoxylated glycerol borates; and glycerides and sucrose esters of fatty acids.

Examples of suitable anionic surface active agents include:

aryl sulfonate salts, especially alkylbenzenesulfonates and alkylnaphthalenesulfonate, such as sodium isopropylnaphthalenesulfonate, sodium methylenebisnaphthalenesulfonate, and sodium dodecylbenzenesulfonate; phosphates or sulfates of polyoxyethylenealkyl or alkylallyl ethers; β-naphthalenesulfonate-formalin condensate salts; ligninsulfonates, such as sodium ligninsulfonate; polymer surfactants of the polycarboxylate and/or polysulfonate type; condensed phosphates, such as sodium hexametaphosphate or sodium tripolyphosphate; salts of higher fatty acids, i.e. soaps, e.g. sodium oleate; salts, e.g. sodium and calcium salts, of sulfonic acids and the acids themselves, e.g. ligninsulfonic acid, and or alkyl sulfonate salts, especially sodium dialkyl sulfosuccinates, such as sodium dioctyl sulfosuccinate or sodium 2-ethylhexenesulfonate and equivalent salts with metals other than sodium; salts, e.g. sodium, ammonium and amine salts, of polyoxyethylene alkyl aryl ether sulfates or of polyoxyethylene alkyl ether sulfates or the free acids; or salts of polyoxyethylene alkyl aryl ether phosphates or of polyoxyethylene alkyl phosphates; and alkyl sulfate salts, such as sodium lauryl sulfate or oleyl sulfate amine salt.

Examples of suitable cationic surfactants include:

the higher aliphatic amines and ethylene oxide condensates with such amines; quaternary ammonium salts, e.g. chlorides; N-alkylamine acetates; and N-alkylamine oxides;

Examples of amphoteric surfactants include betaines and amino acid-type surfactants.

Moreover, the compositions of the present invention may be used in combination with high molecular weight compounds or other formulation agents, for example: protective colloids, such as casein, gelatin, gum arabic, albumin, glue, sodium alginate, carboxymethylcellulose, methylcellulose, hydroxyethylcellulose or polyvinyl alcohol; dispersing agents, such as sodium polyphosphate; inorganic dispersing agents, such as bentonite or veegum; stabilizers; binding agents; and anti-freezing agents. For wider applicability and labor saving, the composition of the invention can, if desired, be combined with one or more other agrochemicals, e.g. fungicides, insecticides, herbicides, plant growth regulators and fertilizers.

The above-mentioned carriers and various auxiliary agents may be used alone or in any desired combination, depending upon the type of preparation, the application and other factors. Similar factors will also be of importance in determining the concentration of the active compound in the formulation. In general terms, we prefer that the compositions of the present invention should contain one part by weight of 3-hydroxy-5-methylisoxazole and from 0.01 to 10 parts by weight, more preferably from 0.1 to 1 parts by weight, of the antimicrobial agent(s). The total content of the active ingredients may vary over a wide range and is not critical to the present invention. In general, it will vary depending upon the nature of the formulation. For example:

A liquid formulation, such as an emulsifiable concentrate, may conveniently contain, for example, from 1 to 50%, more preferably from 5 to 50%, by weight of the active compounds and from 5 to 20% by weight of an emulsifying agent, the remainder being a liquid carrier, together with, if required, a corrosion inhibitor.

Oil preparations may conveniently contain from 0.5 to 5% by weight of the active compounds, the remainder being a liquid carrier such as kerosene.

Dusts may conveniently contain from 0.1 to 25%, more preferably from 0.3 to 25%, by weight of the active compounds, the remainder being a solid carrier.

Wettable powders may conveniently contain, for example, from 1 to 90%, preferably from 25 to 80%, by weight of the active compounds, the remainder being a solid carrier and a dispersing and wetting agent, if required, together with a protective colloidal agent, a thixotropic agent and an anti-foaming agent.

Granules may conveniently contain from 0.3 to 35%, more preferably from 0.3 to 25%, by weight of the active compound, a major portion of the remainder being a solid carrier. The active compound is homogeneously admixed with the solid carrier or is adhered to or adsorbed onto the carrier surface; the diameter of each granule is preferably from 0.2 to 1.5 mm.

The soil fungicidal composition of the present invention may be prepared for use by combining the 3-hydroxy-5-methylisoxazole or salt thereof with one or more of the aforementioned antimicrobial agents by conventional means; for example, by simple mixing, if desired with other conventional ingredients, as described above, to give conventional agrochemical formulations. These formulations may be mixed with one or more other active components, such as other fungicides, bactericides, insecticides, acaricides, fertilizers and soil conditioners, as well as, if desired, carriers and/or diluents or formulation aids.

These formulations may be applied to seeds or soil directly or after dilution to a suitable concentration depending on the purpose. If used for hydroponic culture, direct addition to the nutrient solution may be possible. The timing of the application is not particulary critical, and the formulations can be applied at seeding or at transplanting time. No injury will be caused to crops, even if the formulations are applied during crop growing stages.

Many agrochemicals, including 3-hydroxy-5-methylisoxazole, can cause rusting or corrosion of the apparatus used to prepare or apply or store or dispense them. Furthermore, 3-hydroxy-5-methylisoxazole itself is relatively volatile and so will gradually volatilise on storage, which is not viewed favorably by the purchaser. Moreover, 3-hydroxy-5-methylisoxazole and its anhydrous salts readily burn, thus leading to the possibility of a fire hazard. We have now surprisingly discovered that the dihydrate of the calcium salt of 3-hydroxy-5-methylisoxazole is free from these disadvantages, and, in particular, does not cause or promote rusting or corrosion, even when the active compound is employed in the form of a wettable powder or as water-dispersible granules.

3-Hydroxy-5-methylisoxazole has hitherto been employed as dust formulations, dust coating formulations and liquid formulations. However, since 3-hydroxy-5-methylisoxazole has an acidic hydroxy group in its molecule, it exhibits such disadvantages as causing rust and/or corrosion of the apparatus used for preparing these formulations.

Water-dispersible granules have many advantages, such as:

1) they do not give rise to dust when handled;
2) they are not bulky, since the apparent specific gravity is as small as ½ to ⅓ that of wettable powders; and
3) easy preparation of homogenous dispersions is possible by the addition of water. In general, this type of formulation is prepared by adding water to a mixture of the active compound, a filler, a dispersing agent and a binder, forming the mixture into granules, and then drying them and passing them through a sieve. However, since the vapor pressure of 3-hydroxy-5-methylisoxazole is relatively high, i.e. 0.133 Pa at 25° C., there are problems arising from evaporation of the active ingredient in the drying step of this preparation time.

Hitherto, it has not be&n advantageous to use 3-hydroxy-5-methylisoxazole in such water-dispersible granules because it causes rusting and/or corrosion of apparatus, particularly that used to prepare the formulations. However, we have now surprisingly found that the dihydrate of the calcium salt of 3-hydroxy-5-methylisoxazole can overcome these problems.

Thus, in accordance with a further aspect of the present invention there is provided a fungicidal and bacteriocidal composition for agricultural and horticultural use characterised in that it comprises the dihydrate of the calcium salt of 3-hydroxy-5-methylisoxazole.

In a burning test, anhydrous forms of 3-hydroxy-5-methylisoxazole, its sodium salt, its potassium salt and its calcium salt all kindle and burn easily to make a fire when briefly contacted with a slightly live coal.

On the other hand, the dihydrate of the calcium salt of 3-hydroxy-5-methylisoxazole is almost impossible to set fire to and burns only reluctantly.

Furthermore, the dihydrate of the calcium salt of 3-hydroxy-5-methylisoxazole has considerable physicochemical stability and is not hygroscopic at a relative humidity of 80% at 40° C. Moreover, it will not lose its water of crystallization below 40° C., even at a relative humidity of 5%.

When the dihydrate of the calcium salt of 3-hydroxy-5-methylisoxazole is used, no rusting or corrosion of the apparatus is observed during the preparation of agrochemical formulations containing it, and the active ingredient does not evaporate during the drying step involved in the preparation of water dispersible granular formulations. In contrast, the sodium and potassium salts of 3-hydroxy-5-methylisoxazole cannot be used economically because of their strongly hygroscopic nature.

The dihydrate of the calcium salt of 3-hydroxy-5-methylisoxazole can be prepared by reacting a calcium compound with 3-hydroxy-5-methylisoxazole, and then recovering the desired calcium salt of 3-hydroxy-5-methylisoxazole under conditions favoring the formation of the dihydrate. For example, it may be obtained by the following procedure: one part (molar) of calcium hydroxide and 2 parts (molar) of 3-hydroxy-5-methylisoxazole are added to water and dissolved at a relatively high temperature, preferably from 70° to 90° C., more preferably approximately 80° C.; the resulting solution is then filtered whilst still warm, after which the filtrate is cooled to a suitable temperature to promote the formation of crystals of the dihydrate, suitably approximately 0° C.; the depositing crystals are then removed by filtration and dried, for example at 50°–60° C.

It should, however, be noted that these conditions are given only by way of example and that the reaction and separation conditions may be varied widely. The process of the present invention embraces all conditions which will produce the desired dihydrate.

The resulting dihydrate of the calcium salt of 3-hydroxy-5-methylisoxazole is a whitish crystalline substance, and can be formulated into any conventional agrochemical preparation known for 3-hydroxy-5-methylisoxazole itself, for example, it can be formulated as dusts, dust coatings, wettable granules and liquid formulations according to conventional means. If desired, other agrochemicals (for example, fungicides such as metalaxyl, oxadixyl, triadimefon, prochloraz, benomyl and thiophanate-methyl, and insecticides such as furathiocarb, benfuracarb and carbosulfan) can be incorporated in the formulation, as described generally above.

Examples of methods which may be used to prepare the formulations of the present invention are as follows. The same methods may also be used to prepare similar formulations in accordance with the first aspect of the present invention.

A dust formulation can be obtained by mixing the dihydrate of the calcium salt of 3-hydroxy-5-methylisoxazole with a fine powder of a mineral substance, for example, clay, talc or calcium carbonate, preferably less than 45 μm in diameter, after which the mixture is pulverized, preferably using a pulverizer of the swing-hammer type.

A dust coating formulation can be obtained by mixing the dihydrate of the calcium salt of 3-hydroxy-5-methylisoxazole with any other conventional additives, optionally after adding a filler. Examples of fillers which may be employed for the preparation of a dust coating formulation, include: fine dusts of a mineral substance less than 45 μm in diameter, such as clay, talc, calcium carbonate, white carbon or titanium dioxide; a starch derivative, such as starch or an esterified starch; or a sugar, such as dextrin, glucose, fructose or saccharose. Additives which may be used for the preparation of dust coating formulations include surfactants, such as the non-ionic surfactant and anionic surfactants exemplified above; binders and thermoplastic resin powders. Examples of binders which may be employed for maintaining and binding the active ingredients onto the surfaces of seeds, include water-soluble high molecular weight compounds, for example, water-soluble polysaccharides, such as alginic acid and salts thereof, carboxymethylcellulose and salts thereof, methylcellulose, polyvinyl alcohol, sodium polyacrylate, polyethylene oxide, polyvinylpyrrolidone or xanthan gum. Examples of thermoplastic resin powders having a membrane-forming capacity which may be employed include ethylene-vinyl chloride copolymer resin powder, ethylene-vinyl acetate copolymer resin powder and vinyl chloride resin powder. The dust coating formulation may be prepared by combining the active ingredient with one or more of these additives, depending on the purpose of the formulation. In general, the ranges which may be employed are from 10 to 95%, from 0 to 90%, from 0 to 20% and from 0 to 70% for the active ingredient, filler, wet dispersing agent, binder and thermoplastic resin powder respectively.

A water-dispersible granular formulation can be prepared by mixing the dihydrate of the calcium salt of 3-hydroxy-5-methylisoxazole with one or more additives selected from the group consisting of fillers, wet dispersing agents and binders, as described above in relation to the dust coating formulation, and then pulverizing the mixture. The pulverized mixture is then preferably added to an agitating fluidized bed granulator, water is added, and the whole is mixed and granulated, after which it is dried and sieved. The water-dispersible granules usually have a particle diameter from 63 to 1700 μm.

For preparation of the liquid formulation, selection of the solvent is most important. The solvent must have the following properties: it must be capable of dissolving the dihydrate of the calcium salt of 3-hydroxy-5-methylisoxazole; it must not affect the stability of the active ingredient; it must mix well with water; it must have a low phytotoxicity; and it must have a relatively high boiling point. Examples of solvents which satisfy these conditions include ethylene glycol, propylene glycol and dipropylene glycol. The liquid formulation can be prepared by dissolving the dihydrate of the calcium salt of 3-hydroxy-5-methylisoxazole in one or more of the solvents mentioned above or in a mixture of one or more of these solvents with water. During the preparation of the liquid formulation, an antimicrobial agent, such as a lower alkyl (methyl, ethyl, propyl or butyl) ester of para-hydroxybenzoic acid, or 1,2-benzisothiazolin-3-one (B.I.T.) may be added.

The first aspect of the invention is further illustrated by the following non-limiting Examples, in which all parts and percentages are by weight. The antimicrobial agents used are identified by the codes assigned to them above.

EXAMPLE 1

Fifty parts of 3-hydroxy-5-methylisoxazole, 10 parts of Protectol GDA (a Trade name for an antimicrobial agent containing 50% of Compound B-1, a product of BASF Japan Co., Ltd.), 2 parts of Gohsenol GL-05S (a Trade name for a polyvinyl alcohol; a product of Nippon Synthetic Chemical Industry Co., Ltd.) and 38 parts of Carplex #80-S (a Trade name for a hydrated amorphous silicon dioxide; a product of Shionogi & Co., Ltd.) were mixed and pulverized using a hammer mill to obtain a wettable powder formulation of the present invention.

EXAMPLE 2

Fifty parts of 3-hydroxy-5-methylisoxazole, 25 parts of Proxel GXL (a Trade name for an antimicrobial agent containing 20% of Compound B-5, a product of ICI Japan Co., Ltd.), 2 parts of Gohsenol GL-05S and 23 parts of Carplex #80-S were mixed and pulverized using a hammer mill to obtain a wettable powder formulation of the present invention.

EXAMPLE 3

Four parts of 3-hydroxy-5-methylisoxazole, 4 parts of Protectol GDA, 4 parts of Carplex #80-S and 88 parts of Zeeklite NG (a Trade name for a fine dust containing kaolinite and cesosite as the main ingredients; a product of Zeeklite Co., Ltd.) were mixed and pulverized using a hammer mill to obtain a dust formulation of the present invention.

EXAMPLE 4

Four parts of 3-hydroxy-5-methylisoxazole, 0.5 part of Protectol DMT (a Trade name for an antimicrobial agent containing 100% of Compound B-2, a product of BASF Japan Co., Ltd.) and 95.5 parts of Zeeklite NG were mixed and pulverized using a hammer mill to obtain a dust formulation of the present invention.

EXAMPLE 5

Four parts of 3-hydroxy-5-methylisoxazole, 5 parts of Protectol GL40 (a Trade name for an antimicrobial agent containing 40% of Compound B-3, a product of BASF Japan Co., Ltd.), 5 parts of Carplex #80 and 86 parts of Zeeklite NG were mixed and pulverized using a hammer mill to obtain a dust formulation of the present invention.

EXAMPLE 6

Four parts of 3-hydroxy-5-methylisoxazole, 2.5 parts of Protectol KLC 80 (a Trade name for an antimicrobial agent containing 80% of Compound B-4, a product of BASF Japan Co., Ltd.), 2.5 parts of Carplex #80 and 91 parts of Zeeklite NG were mixed and pulverized using a hammer mill to obtain a dust formulation of the present invention.

EXAMPLE 7

Four parts of 3-hydroxy-5-methylisoxazole, 10 parts of Proxel GLX, 10 parts of Carplex #80 and 76 parts of Zeeklite NG were mixed and pulverized using a hammer mill to obtain a dust formulation of the present invention.

EXAMPLE 8

Four parts of 3-hydroxy-5-methylisoxazole, 2 parts of Compound B-6 and 94 parts of Zeeklite NG were mixed and pulverized using a hammer mill to obtain a dust formulation of the present invention.

EXAMPLE 9

Four parts of 3-hydroxy-5-methylisoxazole, 2 parts of Compound B-7 and 94 parts of Zeeklite NG were mixed and pulverized using a hammer mill to obtain a dust formulation of the present invention.

EXAMPLE 10

Four parts of 3-hydroxy-5-methylisoxazole, 2 parts of Compound B-8 and 94 parts of Zeeklite NG were mixed and pulverized using a hammer mill to obtain a dust formulation of the present invention.

EXAMPLE 11

Four parts of 3-hydroxy-5-methylisoxazole, 2 parts of Mekkings P (a Trade name for an antimicrobial agent containing 99% of the propyl ester of Compound B-9, a product of Ueno Seiyaku Co., Ltd.) and 94 parts of Zeeklite NG were mixed and pulverized using a hammer mill to obtain a dust formulation of the present invention.

EXAMPLE 12

Ten parts of 3-hydroxy-5-methylisoxazole, 20 parts of Protectol GDA and 70 parts of N-methylpyrrolidone were mixed and dissolved to obtain a liquid formulation of the present invention.

EXAMPLE 13

Ten parts of 3-hydroxy-5-methylisoxazole, 50 parts of Proxel GLX and 40 parts of Solfit (a Trade name for a product of Kurare Co., Ltd.) were mixed and dissolved to obtain a liquid formulation of the present invention.

EXAMPLE 14

A mixture of 97.5 parts of Zeeklite NG, 2 parts of Gohsenol GL-05S and 0.5 part of Neocol YSK (a Trade name for a product of Dai-ichi Kogyo Seiyaku Co., Ltd.) was mixed with sufficient water to allow it to be kneaded. It was then passed through a pelleting machine (0.9 mm screen diameter) to form granules, which were dried at 110° C. to obtain a carrier for granule formulation of diameter from 0.3 to 1.7 mm.

Separately, 4 parts of 3-hydroxy-5-methylisoxazole, 2 parts of Protectol GDA and 7 parts of propylene glycol were mixed and dissolved, and then adsorbed onto the carrier for granule formulation prepared as described above to prepare a granular formulation of the present invention.

EXAMPLE 15

Four parts of 3-hydroxy-5-methylisoxazole, 5 parts of Proxel GXL and 5 parts of N,N-dimethylformamide were mixed and dissolved, and then adsorbed onto 86 parts of Kagalite No. 2 (a Trade name for a product of Silver Sangyo Co. Ltd.) to prepare a granular formulation of the present invention.

EXAMPLE 16

Four parts of the calcium salt of 3-hydroxy-5-methylisoxazole, 4 parts of Protectol GDA, 4 parts of Carplex #80 and 88 parts of Zeeklite NG were mixed and dissolved, and then pulverized using a hammer mill to prepare a dust formulation of the present invention.

EXAMPLE 17

Ten parts of 3-hydroxy-5-methylisoxazole, 20 parts of Protectol GDA, 50 parts of Proxel GXL and 20 parts of Solfit were mixed and dissolved to obtain a liquid formulation of the present invention.

EXAMPLE 18

Fifty parts of the calcium salt of 3-hydroxy-5-methylisoxazole, 10 parts of Protectol GDA, 2 parts of Gohsenol GL-05S (a Trade name for a product of Nippon Synthetic Chemical Industry Co., Ltd.) and 38 parts of Carplex #80-S were mixed and pulverized using a hammer mill to obtain a wettable powder formulation of the present invention.

EXAMPLE 19

Fifty parts of the calcium salt of 3-hydroxy-5-methylisoxazole, 25 parts of Proxel GXL, 2 parts of Gohsenol GL-05S and 23 parts of Carplex #80-S were mixed and pulverized using a hammer mill to obtain a wettable powder formulation of the present invention.

EXAMPLE 20

Four parts of 3-hydroxy-5-methylisoxazole, 2 parts of Protectol TOE (a Trade name for an antimicrobial agent containing 100% of Compound B-10, a product of BASF Japan Co., Ltd.) and 94 parts of Zeeklite NG were mixed and pulverized using a hammer mill to obtain a dust formulation of the present invention.

EXAMPLE 21

5.2 parts of the dihydrate of the calcium salt of 3-hydroxy-5-methylisoxazole (prepared as described in Example 1A), 4 parts of Protectol GDA, 4 parts of Carplex #80 and 86.8 parts of Zeeklite NG were mixed and pulverized by a hammer mill to prepare a dust formulation of the present invention.

EXAMPLE 22

Sixty five parts of the dihydrate of the calcium salt of 3-hydroxy-5-methylisoxazole (prepared as described in Example 1A), 10 parts of Protectol GDA, 2 parts of Gohsenol GL-05S and 23 parts of Carplex #80-S were mixed and pulverized by a hammer mill to obtain a wettable powder formulation of the present invention.

EXAMPLE 23

Sixty five parts of the dihydrate of the calcium salt of 3-hydroxy-5-methylisoxazole (prepared as described in Example 1A), 25 parts of Proxel GXL, 2 parts of Gohsonol GL-05S and 8 parts of Carplex #80-S were mixed and pulverized by a hammer mill to obtain a wettable powder fromulation of the present invention.

COMPARATIVE EXAMPLE 1

Using 50 parts of 3-hydroxy-5-methylisoxazole, 2 parts of Gohsenol GL-05S and 48 parts of Carplex #80-S, a wettable powder formulation was obtained by following a similar procedure to that described in Example 1 and Example 2.

COMPARATIVE EXAMPLE 2

Using 10 parts of Protectol GDA, 2 parts of Gohsenol GL05S and 88 parts of Carplex #80-S, a wettable powder formulation was obtained by following a similar procedure to that described in Example 1.

COMPARATIVE EXAMPLE 3

Using 25 parts of Proxel GXL, 2 parts of Gohsenol GL-05S and 73 parts of Carplex #80-S, a wettable powder formulation was obtained by following a similar procedure to that described in Example 2.

COMPARATIVE EXAMPLE 4

Using 4 parts of 3-hydroxy-5-methylisoxazole and 96 parts of Zeeklite NG, a dust formulation was obtained by following a similar procedure to that described in Example 3.

COMPARATIVE EXAMPLE 5

Using 4 parts of Protectol GDA, 4 parts of Carplex #80 and 92 parts of Zeeklite NG, a dust formulation was obtained by following a similar procedure to that described in Example 3.

COMPARATIVE EXAMPLE 6

Using 0.5 part of Protectol DMT and 99.5 parts of Zeeklite NG, a dust formulation was obtained by following a similar procedure to that described in Example 4.

COMPARATIVE EXAMPLE 7

Using 5 parts of Protectol GL40, 5 parts of Carplex #80 and 90 parts of Zeeklite NG, a dust formulation was obtained by following a similar procedure to that described in Example 5.

COMPARATIVE EXAMPLE 8

Using 2.5 parts of Protectol KLC 80, 2.5 parts of Carplex #80 and 95 parts of Zeeklite NG, a dust formulation was obtained by following a similar procedure to that described in Example 6.

COMPARATIVE EXAMPLE 9

Using 10 parts of Proxel GXL, 10 parts of Carplex #80 and 80 parts of Zeeklite NG, a dust formulation was obtained by following a similar procedure to that described in Example 7.

COMPARATIVE EXAMPLE 10

Using 2 parts of Compound B-6 and 98 parts of Zeeklite NG, a dust formulation was obtained by following a similar procedure to that described in Example 8.

COMPARATIVE EXAMPLE 11

Using 2 parts of Compound B-7 and 98 parts of Zeeklite NG, a dust formulation was obtained by following a similar procedure to that described in Example 9.

COMPARATIVE EXAMPLE 12

Using 2 parts of Compound B-8 and 98 parts of Zeeklite NG, a dust formulation was obtained by following a similar procedure to that described in Example 10.

COMPARATIVE EXAMPLE 13

Using 2 parts of Mekkings P and 98 parts of Zeeklite NG, a dust formulation was obtained by following a similar procedure to that described in Example 11.

COMPARATIVE EXAMPLE 14

Using 10 parts of 3-hydroxy-5-methylisoxazole and 90 parts of Solfit, a liquid formulation was obtained by following a similar procedure to that described in Example 13.

COMPARATIVE EXAMPLE 15

Using 20 parts of Protectol GDA and 80 parts of N-methylpyrrolidone, a liquid formulation was obtained by following a similar procedure to that described in Example 12.

COMPARATIVE EXAMPLE 16

Using 50 parts of Proxel GXL and 50 parts of Solfit, a liquid formulation was obtained by following a similar procedure to that described in Example 13.

COMPARATIVE EXAMPLE 17

Using 4 parts of 3-hydroxy-5-methylisoxazole, 8 parts of N,N-dimethylformamide and 88 parts of Kagalite No. 2, a granular formulation was obtained by following a similar procedure to that described in Example 15.

COMPARATIVE EXAMPLE 18

Using 2 parts of Protectol GDA, 7 parts of propylene glycol and 91 parts of the carrier for a granule formulation obtained as described in Example 14, a granular formulation was obtained by following a similar procedure to that described in Example 14.

COMPARATIVE EXAMPLE 19

Using 5 parts of Proxel GXL, 5 parts of N,N-dimethylformamide and 90 parts of Kagalite No. 2, a granular formulation was obtained by following a similar procedure to that described in Example 15.

COMPARATIVE EXAMPLE 20

Using 4 parts of the calcium salt of 3-hydroxy-5-methylisoxazole and 96 parts of Zeeklite NG, a dust formulation was obtained by following a similar procedure to that described in Example 16.

COMPARATIVE EXAMPLE 21

Using 50 parts of the calcium salt of 3-hydroxy-5-methylisoxazole, 2 parts of Gohsenol GL-05S and 48 parts of Carplex 80-S, a wettable powder formulation was obtained by following a similar procedure to that described in Example 18 and Example 19.

COMPARATIVE EXAMPLE 22

Using 2 parts of Protectol TDE and 98 parts of Zeeklite NG, a dust formulation was obtained by following a similar procedure to that described in Example 20.

COMPARATIVE EXAMPLE 23

Using 5.2 parts of the dihydrate of the calcium salt of 3-hydroxy-5-methylisoxazole (prepared as described in Example 1A) and 94.8 parts of Zeeklite NG, a dust formulation was obtained by following a similar procedure to that described in Example 22.

COMPARATIVE EXAMPLE 24

Using 65 parts of the dihydrate of the calcium salt of 3-hydroxy-5-methylisoxazole (prepared as described in Example 1A), 2 parts of Gohsonol GL-05S and 33 parts of Carplex #80-S, a wettable powder formulation was obtained by following a similar procedure to that described in Example 23 and 24.

ACTIVITY DATA

The composition of the present invention can greatly enhance and prolong the disease controlling effect and physiological activities of 3-hydroxy-5-methylisoxazole and salts thereof, and can improve the residual effect. These properties permit the compositions of the present invention to be used in amounts corresponding to lower doses of 3-hydroxy-5-methylisoxazole or salt thereof than was hitherto possible.

EXPERIMENT 1

Control of Rice seedling damping-off (wettable powder)

A culture of pythium graminicola (previously cultivated with shaking in a potato-sucrose medium) was homogenized using a blender to obtain a suspension of its hyphae. This suspension was mixed with sterilized soil. The soil sample inoculated with the pathogen was packed in a small plastic nursery box, 20×20 cm, 3 cm deep. Rice seeds (var.: Koshihikari), which had been previously immersed for germination, were then coated with a known amount of one of the wettable powder formulations prepared in Examples 1, 2, 18 and 19, and Comparative Examples 1, 2, 3 and 21, and then immediately the seeds were sown at the rate of 30 g of dry rough rice seeds per box. The seedlings were grown in a glass-house kept at 20° C. in the daytime and 15° C. in the night. The diseased area resulting from the rice seedling damping-off was measured 2 or 3, and 5 weeks after sowing. The inhibition of growth of the rice seedlings was examined 2 weeks after sowing by comparison with a control free from the pathogen.

As is shown in Tables 1 and 2, the controlling effects of 3-hydroxy-5-methylisoxazole and the calcium salt of 3-hydroxy-5-methylisoxazole continued for about 2 to 3 weeks. Then symptoms of the disease began to occur rapidly and vigorous symptoms were observed after 5 weeks. When the plants were treated with 3-hydroxy-5-methylisoxazole, the calcium salt of 3-hydroxy-5-methylisoxazole, Compound B-1 or Compound B-5 alone, the activity was found to be very weak. However, when 3-hydroxy-5-methylisoxazole or the calcium salt of 3-hydroxy-5-methylisoxazole was combined with Compound B-1 or Compound B-5, no infection of the rice seedlings was observed even after 5 weeks. The residual effectiveness of the 3-hydroxy-5-methylisoxazole or the calcium salt of 3-hydroxy-5-methylisoxazole was remarkably enhanced, and a surprising activity was exhibited. No phytotoxicity, such as growth inhibition, was observed in the rice seedlings after treatment with the composition of the present invention at any dose. On the contrary, elongation of the roots was promoted and healthy seedlings were obtained. After treatment with 3-hydroxy-5-methylisoxazole at a high concentration (1% by weight of seeds), strong phytotoxicity (inhibited germination, inhibited growth) was observed, however after treatment with the calcium salt of 3-hydroxy-5-methylisoxazole, at the same concentration, no phytotoxicity was observed.

In the following Tables, the inhibition of rice seedling growth is reported using the following symbols:

−: No growth inhibition is observed.

±: Slight growth inhibition is observed.

+: Seedling height is no more than ⅔ of normal

++: Seedling height is no more than ⅓ of normal

+++: No germination

In the following Tables, Compound A is 3-hydroxy-5-methylisoxazole, Compound C is the calcium salt of 3-hydroxy-5-methylisoxazole (anhydrous) and Compound D is the dihydrate of the calcium salt of 3-hydroxy-5-methylisoxazole.

TABLE 1

|  | Test compound Dosage* | | Area affected by rice seedling damping-off (%) | | Rice seedling growth inhibition |
|---|---|---|---|---|---|
|  |  |  | 2 weeks after sowing | 5 weeks after sowing |  |
|  | (Compound A) | (Compound B-1) |  |  |  |
| Example No. 1 | 0.05 | 0.005 | 0 | 0 | − |
|  | 0.1 | 0.01 | 0 | 0 | − |
|  | 0.2 | 0.02 | 0 | 0 | − |
|  | 0.4 | 0.04 | 0 | 0 | − |
|  | (Compound A) | (Compound B-5) |  |  |  |
| Example No. 2 | 0.05 | 0.005 | 0 | 0 | − |
|  | 0.1 | 0.01 | 0 | 0 | − |
|  | 0.2 | 0.02 | 0 | 0 | − |
|  | 0.4 | 0.04 | 0 | 0 | − |
|  | (Compound A) |  |  |  |  |
| Comp. Example No. 1 | 0.05 |  | 15 | 90 | − |
|  | 0.1 |  | 0 | 50 | − |
|  | 0.2 |  | 0 | 30 | − |
|  | 0.4 |  | 0 | 10 | − |
|  | (Compound B-1) | | | | |

TABLE 1-continued

| Test compound Dosage* | | Area affected by rice seedling damping-off (%) | | Rice seedling growth inhibition |
|---|---|---|---|---|
| | | 2 weeks after sowing | 5 weeks after sowing | |
| Comp. Example No. 2 | 0.005 | 50 | 100 | — |
| | 0.01 | 40 | 100 | — |
| | 0.02 | 25 | 90 | — |
| | 0.04 | 15 | 70 | — |
| | (Compound B-5) | | | |
| Comp. Example No. 3 | 0.01 | 30 | 100 | — |
| | 0.02 | 20 | 80 | — |
| | 0.04 | 10 | 60 | — |
| untreated control | | 50 | 100 | — |

*The dosage is the amount of active compound expressed as a percentage of the weight of the seeds.

TABLE 2

| Test compound Dosage* | | Area affected by rice seedling damping-off (%) | | Rice seedling growth inhibition |
|---|---|---|---|---|
| | | 3 weeks after sowing | 5 weeks after sowing | |
| | (Compound C) | (Compound B-1) | | |
| Example No. 18 | 0.25 | 0.025 | 0 | 0 | — |
| | 0.5 | 0.05 | 0 | 0 | — |
| | 1.0 | 0.01 | 0 | 0 | — |
| | (Compound C) | (Compound B-5) | | | |
| Example No. 19 | 0.25 | 0.025 | 0 | 0 | — |
| | 0.5 | 0.05 | 0 | 0 | — |
| | 1.0 | 0.2 | 0 | 0 | — |
| | (Compound A) | | | | |
| Comp. Example No. 1 | 0.25 | | 15 | 80 | — |
| | 0.5 | | 0 | 60 | ± |
| | 1.0 | | (Not judged due to no germination) | | +++ |
| | (Compound B-1) | | | | |
| Comp. Example No. 2 | 0.025 | | 40 | 100 | — |
| | 0.05 | | 30 | 80 | — |
| | 0.1 | | 20 | 70 | — |
| | (Compound B-5) | | | | |
| Comp. Example No. 3 | 0.05 | | 30 | 90 | — |
| | 0.1 | | 25 | 80 | — |
| | (Compound C) | | | | |
| Comp. Example No. 21 | 0.25 | | 20 | 80 | — |
| | 0.5 | | 0 | 50 | — |
| | 1.0 | | 0 | 20 | — |
| Untreated control | | | 40 | 100 | — |

*as Table 1

EXPERIMENT 2

Control of Rice seedling damping-off (Dust formulation)

Infested soil (the same as was used in Experiment 1) was treated with each of the dust formulations prepared in Examples 3 to 11, 18, 20 and 21, and Comparative Examples 4 to 13 and 21 to 23 over the whole soil layer. Seeding, cultivation and evaluation were carried out as described in Experiment 1.

As is shown in Table 3, 3-hydroxy-5-methylisoxazole, the calcium salt of 3-hydroxy-5-methylisoxazole or the dihydrate of the calcium salt of 3-hydroxy-5-methylisoxazole exhibited poor residual effectiveness when applied alone. Also all of the antibacterial ingredients used in this test had a weak controlling effect when applied alone. However, when 3-hydroxy-5-methylisoxazole, the calcium salt of 3-hydroxy-5-methylisoxazole or the dihydrate of the calcium salt of 3-hydroxy-5-methylisoxazole were combined with any of the antibacterial ingredients, the controlling effect of 3-hydroxy-5-methylisoxazole, the calcium salt of 3-hydroxy-5-methylisoxazole or the dihydrate of the calcium salt of 3-hydroxy-5-methylisoxazole was greatly increased including its residual effectiveness. In addition, no phytotoxicity, such as rice seedling growth inhibition, was observed after application of any of the other compositions than those combined with Compound B-8. On the contrary, growth of the roots was promoted and healthy seedlings were obtained. The results are shown in Table 3.

TABLE 3

| Test compound Dosage* | | Area affected by rice seedling damping-off (%) | | Rice seedling growth inhibition |
|---|---|---|---|---|
| | | 2 weeks after sowing | 5 weeks after sowing | |
| | (Compound A) | (Compound B-1) | | |
| Example No. 3 | 10 | 5 | 0 | 0 | — |
| | 20 | 10 | 0 | 0 | — |
| | (Compound A) | (Compound B-2) | | | |
| Example No. 4 | 10 | 5 | 0 | 30 | — |
| | 20 | 10 | 0 | 10 | — |
| | (Compound A) | (Compound B-3) | | | |
| Example No. 5 | 10 | 5 | 5 | 60 | — |
| | 20 | 10 | 0 | 0 | — |
| | (Compound A) | (Compound B-4) | | | |
| Example No. 6 | 10 | 5 | 0 | 70 | — |
| | 20 | 10 | 0 | 10 | — |
| | (Compound A) | (Compound B-5) | | | |
| Example No. 7 | 10 | 5 | 0 | 0 | — |
| | 20 | 10 | 0 | 0 | — |
| | (Compound A) | (Compound B-6) | | | |
| Example No. 8 | 10 | 5 | 10 | 50 | — |
| | 20 | 10 | 0 | 20 | — |
| | (Compound A) | (Compound B-7) | | | |
| Example | 10 | 5 | 10 | 30 | — |

TABLE 3-continued

| | Test compound Dosage* | | Area affected by rice seedling damping-off (%) | | Rice seedling growth inhibition |
|---|---|---|---|---|---|
| | | | 2 weeks after sowing | 5 weeks after sowing | |
| No. 9 | 20 (Compound A) | 10 (Compound B-8) | 0 | 30 | — |
| Example No. 10 | 10 20 (Compound A) | 5 10 (Compound B-9) | 0 0 | 40 30 | — |
| Example No. 11 | 10 20 (Compound A) | 5 10 (Compound B-1) | 10 0 | 40 35 | — |
| Example No. 16 | 10 20 (Compound A) | 5 10 (Compound B-10) | 0 0 | 0 0 | — — |
| Example No. 20 | 10 20 (Compound D) | 5 10 (Compound B-1) | 0 0 | 15 0 | — |
| Example No. 21 | 10 20 (Compound A) | 5 10 | 0 0 | 0 0 | — |
| Comp. Example No. 4 | 10 20 | | 10 0 | 80 40 | — — |
| | (Compound B-1) | | | | |
| Comp. Example No. 5 | 5 10 | | 40 30 | 100 80 | — |
| | (Compound B-2) | | | | |
| Comp. Example No. 6 | 5 10 | | 40 35 | 100 90 | — |
| | (Compound B-3) | | | | |
| Comp. Example No. 7 | 5 10 | | 40 30 | 100 90 | — |
| | (Compound B-4) | | | | |
| Comp. Example No. 8 | 5 10 | | 50 40 | 90 90 | — |
| | (Compound B-5) | | | | |
| Comp. Example No. 9 | 5 10 | | 25 10 | 100 80 | — |
| | (Compound B-6) | | | | |
| Comp. Example No. 10 | 5 10 | | 50 30 | 100 100 | — |
| | (Compound B-7) | | | | |
| Comp. Example No. 11 | 5 10 | | 50 50 | 100 90 | — |
| | (Compound B-8) | | | | |
| Comp. Example No. 12 | 5 10 | | 40 20 | 100 90 | — + |
| | (Compound B-9) | | | | |
| Comp. Example No. 13 | 5 10 | | 40 30 | 100 80 | — |
| | (Compound C) | | | | |
| Comp. Example No. 20 | 10 20 | | 15 0 | 80 50 | — |
| | (Compound B-10) | | | | |
| Comp. Example No. 22 | 5 10 | | 50 30 | 100 90 | — |
| | (Compound D) | | | | |
| Comp. Example No. 23 | 10 20 | | 18 5 | 80 65 | — |
| Untreated control | | | 50 | 100 | — |

*The dosage is the amount of active compound (mg) per box.

EXPERIMENT 3

Control of Fusarium wilt in cucumber (Liquid formulation)

A suspension of microconidia of *Fusarium oxysporum f. sp. cucumerinum* (which had previously been cultured with shaking in a potato-sucrose medium) was mixed with sterilized soil. The soil sample was packed into a plastic pot (size 2 liters). Cucumber seedlings (var.: Sagami Hanjiro, at the two-leaf stage) were then planted at the rate of 3 cucumbers per pot. Each soil sample in which they were planted was drenched at the rate of 100 ml per pot with a known amount of one of the liquid formulations prepared as described in Examples 12, 13 and 17 and Comparative Examples 14, 15 and 16, after dilution with water. After culture for 3 and 5 weeks in a greenhouse, the number of healty seedlings was determined. The results were averaged over 5 identically treated pots in each case.

As is shown in Table 4, the soil fungicidal composition of the present invention perfectly inhibited the occurrence of Fusarium wilt.

TABLE 4

% of healthy

| No. | Test compound Dosage* | | After 3 weeks seedlings | After 5 weeks | Phyto-toxicity |
|---|---|---|---|---|---|
| | (Compound A) | (Compound B-1) | | | |
| Example 12 | 200 | 200 | 100 | 95 | — |
| | 400 | 400 | 100 | 100 | — |
| | 600 | 600 | 100 | 100 | — |
| | (Compound A) | (Compound B-5) | | | |
| Example 13 | 200 | 200 | 100 | 90 | — |
| | 400 | 400 | 100 | 100 | — |
| | 600 | 600 | 100 | 100 | — |
| | (Cpd. A) | (Cpd. B-1) (Cpd. B-5) | | | |
| Ex. 17 | 200 200 | 200 | 100 | 100 | — |
| | 400 400 | 400 | 100 | 100 | — |
| | (Compound A) | | | | |
| Comp. Example 14 | 200 | | 30 | 0 | — |
| | 400 | | 50 | 10 | — |
| | 600 | | 60 | 10 | — |
| | | (Compound B-1) | | | |
| Comp. Example 15 | | 200 | 25 | 0 | — |
| | | 400 | 25 | 0 | — |
| | | 600 | 30 | 0 | — |
| | | (Compound B-5) | | | |
| Comp. Example 16 | | 200 | 20 | 0 | — |
| | | 400 | 20 | 0 | — |
| | | 600 | 30 | 0 | — |
| Untreated control | | | 20 | 0 | — |

*The dosage is the concentration of active compound (ppm) in the drenching liquid.

EXPERIMENT 4

Control of Sugar beet seedling damping-off
(Granules)

Mycelial cells of *Aphanomyces cochlioides*, including oospores, which had been obtained by culturing the microorganism on a corn meal agar medium to which cholesterol had been added, were homogenized using a blender and mixed with sterilized soil. Each soil sample was packed into a plastic pot (size: 30×40 cm, 20 cm deep). Seeds of sugar beet (var.: Monomidori) were sown at the rate of 60 seeds per pot. After sowing, each of the granule formulations obtained in Examples 14 and 15 and Comparative Examples 17, 18 and 19 was scattered on the surface of the soil sample in the pots. After culture in a greenhouse for 6 weeks, the number of healthy seedlings was determined. The results were averaged over 3 identically treated pots in each case. As is shown in Table 5, the soil fungicidal composition of the present invention exhibited a remarkable activity against damping-off of sugar beet seedlings.

TABLE 5

| No. | Test compound Dosage* | | % of healthy seedlings | Phytotoxicity |
|---|---|---|---|---|
| | (Compound A) | (Compound B-1) | | |
| Example 14 | 10 | 2.5 | 60 | — |
| | 20 | 5 | 90 | — |
| | 40 | 10 | 100 | — |
| | (Compound A) | (Compound B-5) | | |
| Example 15 | 10 | 2.5 | 70 | — |
| | 20 | 5 | 90 | — |
| | 40 | 10 | 100 | — |
| | (Compound A) | | | |
| Comp. Example 17 | 10 | | 30 | — |
| | 20 | | 50 | — |
| | 40 | | 60 | — |
| | | (Compound B-1) | | |
| Comp. Example 18 | | 2.5 | 20 | — |
| | | 5 | 25 | — |
| | | 10 | 25 | — |
| | | (Compound B-5) | | |
| Comp. Example 19 | | 2.5 | 15 | — |
| | | 5 | 20 | — |
| | | 10 | 20 | — |
| Untreated control | | | 20 | — |

*The dosage is the amount (mg) of active compound per pot.

EXPERIMENT 5

Control of Sugar beet seedling damping-off
(Wettable powder)

A procedure similar to that described in Experiment 3 was repeated, in which a soil sample infected with the pathogen was packed in a plastic pot. Sugar beet seeds (var.: Monomidori and Hokkai No. 51) were coated with the wettable powder formulations obtained as described in Examples 18, 19, 22 and 23 and Comparative Examples 1, 2, 3, 21 and 24 together with 2% gum arabic liquid. The coated sugar beet seeds were sown at the rate of 60 seeds per pot. After culture in a greenhouse for 6 weeks, the number of healthy seedlings was determined. The results were averaged over 3 identically treated pots in each case. As is shown in Table 6, the soil fungicidal composition of the present invention exhibited a remarkable activity against damping-off of sugar beet seedlings, and, moreover, no phytotoxicity was observed.

TABLE 6

| | Test compound Dosage* | | Monomidori | | Hokkai 51 | |
|---|---|---|---|---|---|---|
| | | | % of healthy seedlings | Phyto-toxicity | % of healthy seedlings | Phyto-toxicity |
| | (Cpd. C) | (Cpd. B-1) | | | | |
| Ex. 18 | 1.0 | 0.1 | 85 | — | 90 | — |
| | 1.5 | 0.15 | 90 | — | 95 | — |
| | (Cpd. C) | (Cpd. B-5) | | | | |
| Ex. 19 | 1.0 | 0.1 | 80 | — | 88 | — |
| | 1.5 | 0.15 | 90 | — | 95 | — |
| | (Cpd. D) | (Cpd. B-1) | | | | |
| Ex. 23 | 1.0 | 0.1 | 90 | — | 93 | — |
| | 1.5 | 0.15 | 93 | — | 95 | — |
| | (Cpd. D) | (Cpd. B-5) | | | | |

TABLE 6-continued

| | Test compound Dosage* | | Monomidori | | Hokkai 51 | |
|---|---|---|---|---|---|---|
| | | | % of healthy seedlings | Phytotoxicity | % of healthy seedlings | Phytotoxicity |
| Ex. 24 | 1.0<br>1.5<br>(Compound A) | 0.1<br>0.15 | 85<br>95 | –<br>– | 90<br>95 | –<br>– |
| Comp. Ex. 1 | 1.0<br>1.5<br><br>(Compound B-1) | | 37<br>53 | –<br>Delayed growth | 60<br>57 | –<br>Delayed growth |
| Comp. Ex. 2 | 0.1<br>0.15<br>(Compound B-5) | | 8<br>10 | –<br>– | 10<br>14 | –<br>– |
| Comp. Ex. 3 | 0.1<br>0.15<br>(Compound C) | | 7<br>10 | –<br>– | 11<br>13 | –<br>– |
| Comp. Ex. 21 | 1.0<br>1.5<br>(Compound D) | | 47<br>60 | –<br>– | 70<br>80 | –<br>– |
| Comp. Ex. 24 | 1.0<br>1.5 | | 50<br>55 | –<br>– | 75<br>80 | –<br>– |
| Untreated control | | | 5 | – | 8 | – |

*The dosage is the amount of active compound expressed as a percentage of the weight of the seeds.

EXPERIMENT 6

Direct sowing test using rice paddy field soil

Paddy field soil was packed in a plastic box (size, 50 cm×40 cm, 10 cm deep), to a depth of 5 cm; water was added and the soil was levelled. Rice seeds (var.: Koshihikari) which had previously been immersed for germination were coated with a known amount of each of the wettable powder formulations prepared as described in Examples 18 and 19 and in Comparative Examples 1 to 3 and 21, and were then immediately sown in the soil sample to a depth of 2 cm at the rate of 120 seeds per box. Keeping a water depth of 3 cm to 5 cm, the seeds were cultivated for 3 weeks in a greenhouse at 20° C. in the daytime and 15° C. at night. At the end of this time, the proportion of seeds which had become established and the degree of phytotoxicity were determined. As is shown in Table 7, although the percentage of seedlings which had become established was higher in the box treated with the 3-hydroxy-5-methylisoxazole or its calcium salt alone than in the untreated control, this percentage was enormously greater in the boxes in which Compound B-1 or B-5 was combined with the calcium salt of 3-hydroxy-5-methylisoxazole. The rates of seedling establishment in the boxes treated with Compound B-1 or B-5 alone were little different from those in the control. The combined antimicrobial compounds exhibited no phytotoxicity at any dose, nor did 3-hydroxy-5-methylisoxazole itself exhibit any phytotoxicity.

TABLE 7

| | Test compound Dosage* | | Rate of seedling establishment (%) | Phytotoxicity |
|---|---|---|---|---|
| | (Compound C) | (Compound B-1) | | |
| Example 18 | 0.5 | 0.05 | 95 | – |
| | (Compound C) | (Compound B-5) | | |
| Example 19 | 0.5 | 0.05 | 92 | – |
| | (Compound A) | | | |
| Comp. Ex. 1 | 0.5 | | 68 | – |
| | | (Compound B-1) | | |
| Comp. Ex. 2 | | 0.05 | 58 | – |
| | | (Compound B-5) | | |
| Comp. Ex. 3 | | 0.05 | 60 | – |
| | (Compound C) | | | |
| Comp. Ex. 21 | 0.5 | | 72 | – |
| Untreated control | | | 54 | – |

*The dosage is the amount of active compound expressed as a percentage of the weight of the seeds.

EXPERIMENT 7

Algicidal test in solution for hydroponics

Algae were grown in pond water in a greenhouse. A water sample was taken in a 100 ml beaker and to it was added a known concentration of each of the liquid formulations prepared as described in Examples 12 and 13, and in Comparative Examples 14, 15 and 16. After keeping the pond water in the greenhouse for 1 week, the degree of generation of algae was examined.

The results are shown in Table 8, from which it can be seen that the composition of the present invention has a remarkable algicidal effect.

In Table 8, the degree of generation of algae is reported using the following symbols:

–: No generation was observed.

±: Slight generation was observed.

+: Generation was observed.

++: Fair generation was observed.

+++: As much generation was observed as in the control:

TABLE 8

| Test compound Dosage* | | Degree of algal generation |
|---|---|---|
| (Compound A) | (Compound B-1) | |

TABLE 8-continued

| | Test compound Dosage* | | | Degree of algal generation |
|---|---|---|---|---|
| Example 12 | 30<br>100<br>(Compound A) | 30<br>100<br>(Compound B-5) | | –<br>– |
| Example 13 | 30<br>100<br>(Compound A) | 30<br>100<br>(Compound B-1) | (Compound B-5) | –<br>– |
| Example 17 | 10<br>30<br>(Compound A) | 10<br>30 | 10<br>30 | –<br>– |
| Comp. Example 14 | 30<br>100<br>(Compound B-1) | | | +<br>± |
| Comp. Example 15 | 30<br>100<br>(Compound B-5) | | | ++<br>++ |
| Comp. Example 16 | 30<br>100 | | | +++<br>++ |
| Untreated control | | | | +++ |

*The dosage is the concentration of the active compound in ppm.

EXAMPLE 1A 5.7 kg of water, 0.57 kg of calcium hydroxide and 1.4 kg of 3-hydroxy-5-methylisoxazole were added to a 10 liter glass flask, and the mixture was heated to 80° C. until the solids had dissolved. It was then filtered whilst still warm. The filtrate was then cooled to 0° C. The crystals which separated were collected by filtration and dried for 2 hours at 55° C. to obtain 1.0 kg of crude white crystals. These were recrystallized from water and then dried for 2 hours at 55° C. to afford white crystals, melting at 280° C. (with decomposition).

Elemental analysis: Calculated for $C_8H_8N_2O_4Ca.4H_2O$: C, 31.17%; H, 5.23%; N, 9.09%. Found: C, 31.09%; H, 5.24%; N: 9.07%. Infrared Absorption Spectrum (KBr), $v_{max}$ cm$^{-1}$: 3377(s), 3220(w), 1650(w), 1626(s), 1510(s), 1410(s), 1255(s), 1150(s), 1025(s), 900(s) Nuclear Magnetic Resonance spectrum ($D_2O$), δ ppm: 2.11 (3H, doublet, J=0.8 Hz); 5.36 (1H, quartet, J=0.8 Hz). Water content by Karl-Fischer method Calculated (%): 23.37 Found (%): 23.62.

From these analytical data, the compound obtained was confirmed to be the dihydrate of the calcium salt of 3-hydroxy-5-methylisoxazole.

EXAMPLE 2A 6.5 parts by weight of the dihydrate of the calcium salt of 3-hydroxy-5-methylisoxazole (the crude white crystals obtained as described in Example 1; 97.8% purity, calculated as the dihydrate of the calcium salt of 3-hydroxy-5-methylisoxazole) and 93.5 parts by weight of Zeeklite NG (a Trade name for a fine dust containing kaolinite and sericite as the main ingredients; a product of Zeeklite Co., Ltd.) were mixed and then finely powdered, using a hammermill-type pulverizer (Ecksample mill Type KII-1; Product of Fuji Powdal Co., Ltd.), to obtain a dust formulation.

EXAMPLE 3A 64.5 parts by weight of the dihydrate of the calcium salt of 3-hydroxy-5-methylisoxazole (purity 97.8%) and 35.5 parts by weight of Carplex #80 (a Trade name for a hydrated amorphous silicon dioxide; a product of Shionogi & Co., Ltd.) were mixed and then finely powdered, using an Ecksmaple mill Type KII-1, to obtain a dust coating formulation.

EXAMPLE 4A 80.0 parts by weight of the dihydrate of the calcium salt of 3-hydroxy-5-methylisoxazole (purity 98.8%), 19.0 parts by weight of Carplex #80 and 1.0 parts by weight of Gohsenol GL-05S (a Trade name for a polyvinyl alcohol; a product of Nippon Synthetic Chemical Industry Co., Ltd.) were mixed and then finely powdered, using an Ecksample mill Type KII-1, to obtain a dust coating formulation.

EXAMPLE 5A 90.0 parts by weight of the dihydrate of the calcium salt of 3-hydroxy-5-methylisoxazole (purity 98.8%), 7 parts by weight of FARZYM-T (a Trade Name for a denatured starch; a product of Matsutani Chem. Ind. Co., Ltd.) and 3 parts by weight of Neogen Powder (a Trade Name for sodium alkyl[$C_{12}$]benzenesulfonate; a product of Dai-Ichi Kogyo Seiyaku Co., Ltd.) were mixed and then finely powdered, using an Ecksample mill Type KII-1, to obtain a dust coating formulation.

EXAMPLE 6A 50.0 parts by weight of the dihydrate of the calcium salt of 3-hydroxy-5-methylisoxazole (purity 98.8%), 45.0 parts by weight of Caoline KCS (a Trade Name for a fine powder of kaolinite clay; a product of Matsumura Ind. Co., Ltd.) and 5.0 parts by weight of Labelin FAN (a Trade Name for a sodium salt of a condensation product of naphthalenesulfonic acid and formalin; a product of Dai-Ichi Kogyo Seiyaku Co., Ltd.) were mixed, and the mixture was pulverized, using an Ecksample mill Type KII-1, to obtain 1000 g of a pulverized product. This product was charged into a Vertical Granulator Type FM-VG-05 (an agitating granulator; a product of Powrex Co. Ltd.), 150 g of water were added, mixed with stirring for 3 minutes at a blade speed of 800 rpm and at a cross screw speed of 3000 rpm. The granular product obtained was dried using a fluidized bed dryer, Mizet Dryer Type MD-B-400 (a product of Fuji Powdal Co., Ltd.) until at an inlet air temperature of 60° C., an outlet air temperature of 50° C. was achieved. The product was sieved to select particles of diameter from 105 μm to 840 μm, and thus to obtain the desired water-dispersible granular formulation.

EXAMPLE 7A 26 parts by weight of the dihydrate of the calcium salt of 3-hydroxy-5-methylisoxazole (purity 97.8%) were added to a mixture of 53 parts by weight of ethylene glycol and 21 parts by weight of water and dissolved, to obtain a liquid formulation.

COMPARATIVE EXAMPLE 1A

A procedure similar to that described in Example 6A was repeated, except that 50.0 parts by weight of the dihydrate of the calcium salt of 3-hydroxy-5-methylisoxazole (purity 98.8%) were replaced by 32.0 parts by weight of 3-hydroxy-5-methylisoxazole (purity 98.7%) and that 45.0 parts by weight of Caoline KCS were replaced by 63.0 parts by weight of Caoline KCS, a water-dispersible granular formulation was obtained.

ACTIVITY DATA

EXPERIMENT 1A

Evaporation of active compound in the drying process

The theoretical content of active compounds in the products of Example 6A and Comparative Example 1A were compared to the actual content of active compound by measuring the actual content of active compound both before and after the drying process using a fluidized bed dryer and described in Example 6A. The theoretical and actual contents of the active compounds were calculated without regard to the water content because the water content was less than 1.0%.

In the products of Example 6A and Comparative Example 1A, when the water content of the samples was 1.5% or more, caking (where particles adhered to each other) was observed during storage of the water-dispersible granular formulation. To maintain a satisfactory quality, it is necessary to have a water content less than 1.0%.

The water content of the samples was measured as follows.

About 5 g of each sample was allowed to stand for 48 hours in a desiccator containing phosphorus pentoxide at ambient temperature, and the difference between the weight before and after standing in the desiccator was assumed to be the water content. On standing for 48 hour in a desiccator, hardly any evaporation of the active compound occurred because phosphorus pentoxide only absorbs water and does not absorb 3-hydroxy-5-methylisoxazole. Accordingly, the content of active compound after standing in a desiccator is almost the same as that before.

The content of the active compound, the dihydrate of the calcium salt of 3-hydroxy-5-methylisoxazole in the composition of Example 6A or 3-hydroxy-5-methylisoxazole itself in the composition of Comparative Example 1A, was measured as follows.
3-Hydroxy-5-methylisoxazole About 0.7 g of the sample was extracted with 50 ml of methanol. 5 ml of this solution were charged into a 50 ml Erlenmeyer flask, 5 ml of a methanolic solution containing 10 mg of phthalic acid, 1.0 ml of 0.1N aqueous sulfuric acid and 19 ml of water (for use as an internal standard) were then added to the flask. 5 μl of this solution was injected into a high performance liquid chromatography (HPLC) column. The eluted active compound and phthalic acid were detected and quantified with an ultraviolet monitor (240 nm) and a digital integrator. A calibration curve prepared from standard solutions was used in order to determine the amount of the active compound in the sample.

HPLC conditions: column: 4.6×250 mm Zorbax ODS (Trade Mark) Mobil phase: methanol, water and 1% phosphoric acid, in a ratio of 30:68:2 by volume; Flow rate: 1 ml/minute.
Dihydrate of the calcium salt of 3-hydroxy-5-methylisoxazole As the dihydrate of the calcium salt of 3-hydroxy-5-methylisoxazole is changed to 3-hydroxy-5-methylisoxazole in an acidic solution, the analytical method for this compound is the same as that for 3-hydroxy-5-methylisoxazole. The percentage content (D %) of the dihydrate of the calcium salt is calculated as follows;

$$D\% = A \times B / C$$

where
- A: content of 3-hydroxy-5-methylisoxazole (wt %);
- B: molecular weight of the dihydrate of the calcium salt of 3-hydroxy-5-methylisoxazole;
- C: molecular weight of 3-hydroxy-5-methylisoxazole.

The "remaining rate" means the content of active compound after the drying process expressed as a percentage of the content of active compound before the drying process. The theoretical content of active compound after the drying process was 49.4% and 31.6% in Example 6A and Comparative Example 1A, respectively.

The results are shown in the following Table 9.

TABLE 9

|  | Example 6A | Comp. Example 1A |
| --- | --- | --- |
| Water content (%) | 0.9 | 0.9 |
| Active cpd. content (%) | 49.4 | 26.3 |
| Remaining rate | 100.0 | 83.2 |

In Example 6A, no evaporation of the active compound was observed during the drying process, but in Comparative Example 1A, 16.8% of the active compound was lost during the drying process.

EXPERIMENT 2A 5 g samples of the anhydrous potassium, sodium and calcium salts of 3-hydroxy-5-methylisoxazole and the dihydrate of the calcium salt of 3-hydroxy-5-methylisoxazole were placed on a porcelain dish (10 cm diameter). The compounds were set fire to with a match and their combustibilities were compared. The results were as follows:

1) Potassium salt of 3-hydroxy-5-methylisoxazole (water content: 1.5%): This compound burned explosively with white smoke, and had totally evaporated almost immediately.

2) Sodium salt of 3-hydroxy-5-methylisoxazole (water content: 1.0%): This compound burned explosively with white smoke, and had totally evaporated almost immediately.

3) Calcium salt of 3-hydroxy-5-methylisoxazole (anhydrous): This compound burned vigorously with black smoke.

4) Calcium salt of 3-hydroxy-5-methylisoxazole (dihydrate): Although it sometimes gave off sooty smok, this compound did not burn. Repeated attempts to set fire to it, even as many as 5 times, caused no burning, although it ultimately resulted in evaporation of the compound.

EXPERIMENT 3A 5 g samples of the anhydrous potassium and sodium salts of 3-hydroxy-5-methylisoxazole and the dihydrate of the calcium salt of 3-hydroxy-5-methylisoxazole were placed on a glass dish and allowed to stand in a desiccator kept at a relative humidity of 80% at 40° C. The water content of the anhydrous potassium and sodium salts increased rapidly, and had increased by about 90% after 48 hours. The rate of increase then began to reduce, but the total increase in water content after 96 hours was over 100% (sodium salt) or almost 100% (potassium salt). On the contrary, the water content of the calcium salt dihydrate showed essentially no increase over the whole period of the test (96 hours). From these results, it is clear that the anhydrous potassium and sodium salts of 3-hydroxy-5-methylisoxazole were hygroscopic, however, no hygroscopicity was found in the dihydrate of the calcium salt of 3-hydroxy-5-methylisoxazole. It is also clear that neither the potassium salt nor the sodium salt of 3-hydroxy-5-methylisoxazole forms a stable hydrate.

I claim:

1. A soil fungicidal composition consisting essentially of (a) an effective fungicidal amount of a fungicide selected from the group consisting of 3-hydroxy-5-methylisoxazole and a salt of 3-hydroxy-5-methylisoxazole, in admixture with or in association with (b) an effective antimicrobial amount of an antimicrobial agent, said antimicrobial agent being 1,2-benzisothiazolin-3-one, (c) a carrier and (d) optionally a plant or soil treatment auxiliary agent.

2. The composition of claim 1, wherein the ratio of said fungicide to said antimicrobial agent is from 15:1 to 1:2.

3. The composition of claim 1, wherein the ratio of said fungicide to said antimicrobial agent is from 13:1 to 1:1.

4. The composition of claim 1, wherein the fungicide is 3-hydroxy-5-methylisoxazole.

5. A method of protecting crops, or other plants, soil or other agricultural media from fungal attack by applying to plants, parts of plants, soil or water, which is applied thereof, or to a locus thereof, a composition consisting essentially of (a) an effective fungicidal amount of a fungicide selected from the group consisting of 3-hydroxy-5-methylisoxazole and a salt of 3-hydroxy-5-methylisoxazole, in admixture with or in association with (b) an effective antimicrobial amount of an antimicrobial agent, said antimicrobial agent being 1,2-benzisothiazolin-3-one, (c) a carrier and (d) optionally a plant or soil treatment auxiliary agent.

6. The method of claim 5, wherein the ratio of said fungicide to said antimicrobial agent is from 15:1 to 1:2.

7. The method of claim 5, wherein the ratio of said fungicide to said antimicrobial agent is from 13:1 to 1:1.

8. The method of claim 5, wherein the fungicide is 3-hydroxy-5-methylisoxazole.

* * * * *